(12) United States Patent
Sinz et al.

(10) Patent No.: US 10,197,586 B2
(45) Date of Patent: *Feb. 5, 2019

(54) METHOD OF DETERMINING A HANDOVER POSITION AND LABORATORY AUTOMATION SYSTEM

(71) Applicant: Roche Diagnostics Operations, Inc., Indianapolis, IN (US)

(72) Inventors: Achim Sinz, Waiblingen (DE); Mohammadreza Mahmudimanesh, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,360

(22) Filed: Mar. 29, 2018

(65) Prior Publication Data

US 2018/0217176 A1 Aug. 2, 2018

Related U.S. Application Data

(63) Continuation of application No. PCT/EP2016/073884, filed on Oct. 6, 2016.

(30) Foreign Application Priority Data

Oct. 6, 2015 (EP) .................................... 15188622

(51) Int. Cl.
*G01N 35/04* (2006.01)

(52) U.S. Cl.
CPC ..... *G01N 35/04* (2013.01); *G01N 2035/0406* (2013.01); *G01N 2035/0465* (2013.01); *G01N 2035/0477* (2013.01); *G01N 2035/0491* (2013.01); *G01N 2035/0494* (2013.01)

(58) Field of Classification Search
None
See application file for complete search history.

(56) References Cited

U.S. PATENT DOCUMENTS

| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |

(Continued)

FOREIGN PATENT DOCUMENTS

| CN | 201045617 Y | 4/2008 |
| CN | 102109530 A | 6/2011 |

(Continued)

OTHER PUBLICATIONS

International Search Report dated Dec. 8, 2016 in Application No. PCT/EP2016/073884, 11 pages.

*Primary Examiner* — Kathryn Wright
(74) *Attorney, Agent, or Firm* — Roche Diagnostics Operations, Inc.

(57) ABSTRACT

A method for determining a handover position of a gripping device and to a laboratory automation system being able to perform such a method are presented. A position determining device is used in order to determine a handover position based on magnetic forces of a handover electro-magnetic actuator that is part of a laboratory sample distribution system of the laboratory automation system.

17 Claims, 2 Drawing Sheets

(56) References Cited

U.S. PATENT DOCUMENTS

| | | |
|---|---|---|
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,618,525 B2 | 4/2017 | Malinowski et al. |
| 9,658,241 B2 | 5/2017 | Riether et al. |
| 9,664,703 B2 | 5/2017 | Heise et al. |
| 9,772,342 B2 | 9/2017 | Riether |
| 9,791,468 B2 | 10/2017 | Riether et al. |
| 9,810,706 B2 | 11/2017 | Riether et al. |
| 9,902,572 B2 | 2/2018 | Mahmudimanesh et al. |
| 9,939,455 B2 | 4/2018 | Schneider et al. |
| 9,952,242 B2 | 4/2018 | Riether |
| 9,969,570 B2 | 5/2018 | Heise et al. |
| 9,989,547 B2 | 6/2018 | Pedain |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131310 A1 | 5/2017 | Volz et al. |
| 2017/0138971 A1 | 5/2017 | Heise et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |

(56) References Cited

U.S. PATENT DOCUMENTS

| | | |
|---|---|---|
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0224476 A1 | 8/2018 | Birrer et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 06-26808 A | 6/1989 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

METHOD OF DETERMINING A HANDOVER POSITION AND LABORATORY AUTOMATION SYSTEM

CROSS-REFERENCE TO RELATED APPLICATIONS

This application is a continuation of PCT/EP2016/073884, filed Oct. 6, 2016, which is based on and claims priority to EP 15188622.3, filed Oct. 6, 2015, which is hereby incorporated by reference.

BACKGROUND

The present disclosure relates to a method of determining a handover position of a gripping device and to a laboratory automation system.

Laboratory automation systems typically comprise a laboratory sample distribution system and a number of laboratory stations. Known laboratory sample distribution systems are typically used in such laboratory automation systems in order to transport samples contained in sample containers between different laboratory stations. Such laboratory sample distribution systems provide for a high throughput and for reliable operation.

Laboratory stations are typically placed just beside the laboratory sample distribution system such that samples can be transported to and from the laboratory stations using the laboratory sample distribution system. In order to pick up and return sample containers containing samples to be analyzed or to be processed otherwise, laboratory stations typically comprise or are positioned in the vicinity of respective gripping devices that are able to grip and collect a sample container that is transported by the laboratory sample distribution system. However, it has been found that calibration of such gripping devices is critical because even a small displacement when gripping a sample container can result in malfunction or even in destruction of the sample container. Thus, calibration or teach-in of such gripping devices is typically done manually and is time consuming.

Therefore, there is a need for a system and a method that allows for easier teach-in of gripping devices.

SUMMARY

According to the present disclosure, a method of determining a handover position of a gripping device is presented. The gripping device can be assigned to a laboratory sample distribution system having a transport plane and a plurality of electro-magnetic actuators positioned below the transport plane. The handover position can be assigned to a handover electro-magnetic actuator. The method can comprise grabbing, by the gripping device, a position determining device such that the position determining device is held fixedly by the gripping device. The position determining device can comprise a magnetically active device. The method can also comprise positioning the position determining device, while being held by the gripping device, on the transport plane; activating the handover electro-magnetic actuator such that it generates a magnetic field interacting with a magnetic field generated by the magnetically active device such that an attractive force is applied on the position determining device; moving the position determining device, while being held by the gripping device, by the attractive force to a first position; detecting the first position; and determining the handover position based at least in part on the first position.

In accordance with one embodiment of the present disclosure, a laboratory automation system is presented. The laboratory automation system can comprise a plurality of analyzing stations, a number of gripping devices, and a laboratory sample distribution system. The laboratory sample distribution system can comprise a number of sample container carriers configured to carry one or more sample containers. Each sample container carrier can comprise at least one magnetically active device. The laboratory sample distribution system can also comprise a transport plane configured to support the sample container carriers and a number of electro-magnetic actuators stationary arranged below the transport plane. The electro-magnetic actuators can be configured to move a sample container carrier on top of the transport plane by applying a magnetic force to the sample container carrier. The laboratory sample distribution system can also comprise a control device configured to control the movement of the sample container carriers on top of the transport plane by driving the electro-magnetic actuators such that the sample container carriers move along corresponding transport paths. For each gripping device, a handover electro-magnetic actuator can be assigned out of the number of electro-magnetic actuators. A sample container can be handed over to or from the gripping device while a sample container carrier carrying the respective sample container is positioned above the handover electro-magnetic actuator. The laboratory automation system can also comprise a process control unit. The process control unit can be configured to control the gripping devices and the laboratory sample distribution system such that the above method is performed.

Accordingly, it is a feature of the embodiments of the present disclosure to provide for a system and a method that allows for easier teach-in of gripping devices. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
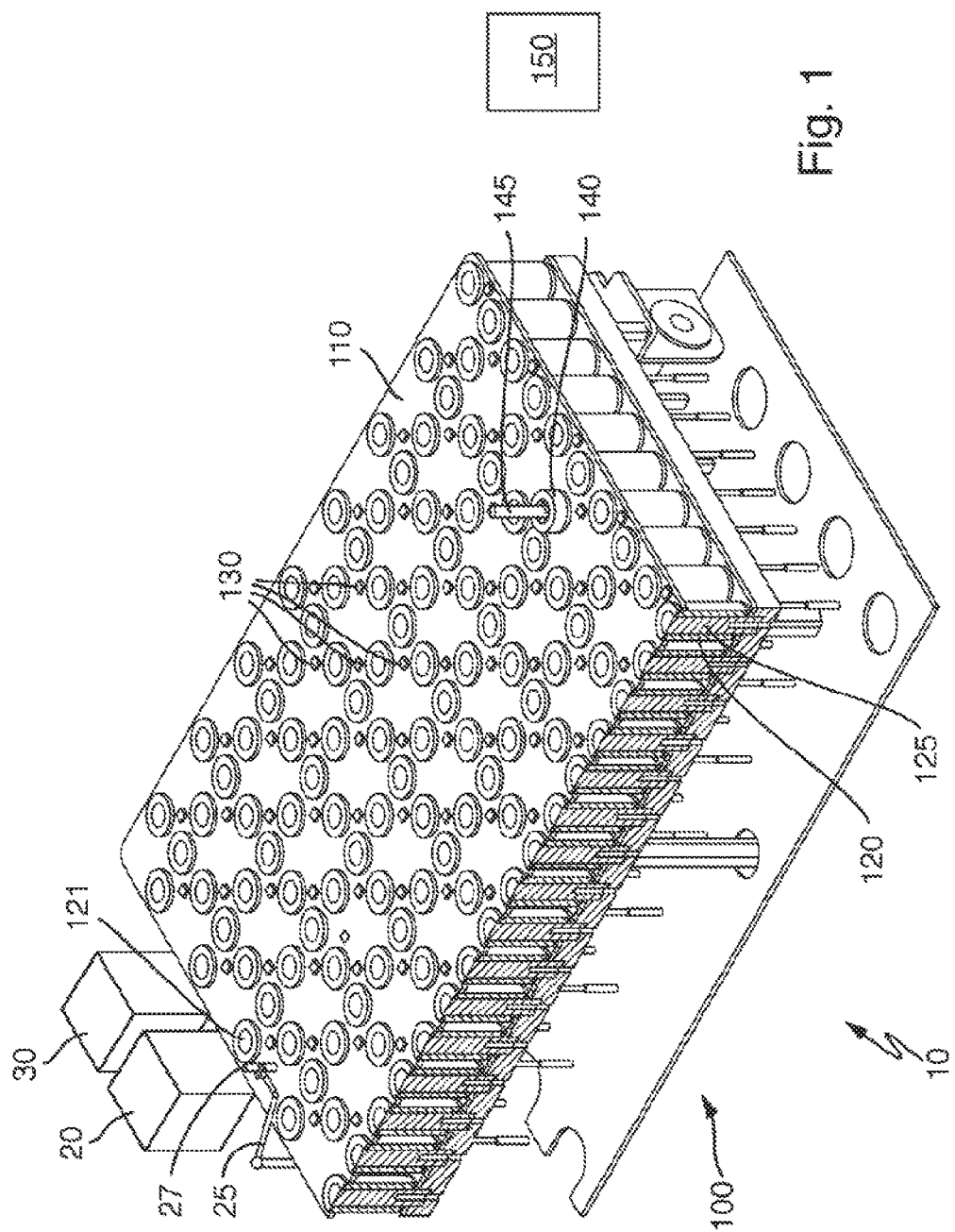
FIG. 1 illustrates a laboratory automation system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method of determining a handover position of a gripping device is disclosed. Such a handover position will typically be used by the gripping device after the method has been performed, for example during everyday operation. In other words, after the handover position has been determined, the gripping device can use (drive to) the determined handover position to remove a sample container from a sample container carrier and/or to insert a sample container into a sample container carrier. The handover position can e.g. be represented by planar i.e. x-y-coordinates denoting a specific position on (in) the transport plane.

The gripping device, e.g. in form of a pick-and-place device, can be assigned to a laboratory sample distribution system having a transport plane and a plurality of electro-magnetic actuators positioned below the transport plane. Typically, such a gripping device can be positioned just beside the laboratory sample distribution system, and specifically beside the transport plane.

The handover position can be assigned to a handover electro-magnetic actuator. The handover electro-magnetic actuator can typically be an electro-magnetic actuator on which a sample container to be gripped by the gripping device can be placed during operation.

The method can comprise gripping, by the gripping device, a position determining device such that the position determining device can be held fixedly by the gripping device. The position determining device can comprise a magnetically active device, e.g. in form of a permanent magnet. The method can also comprise positioning the position determining device, while being held by the gripping device, on top of the transport plane, activating the handover electro-magnetic actuator such that it generates a magnetic field interacting with a magnetic field generated by the magnetically active device such that an attractive force is applied to the position determining device, moving the position determining device, while being held by the gripping device, by the attractive force to a first position, detecting the first position, and determining the handover position based on the first position.

By use of the method, calibration, or teaching, of a gripping device can be done automatically, which can consume less time and can be less error-prone than manual calibration.

It can be noted that when moving the position determining device while being held by the gripping device by the attractive force to the first position, the gripping device can typically allow for movement of the position determining device in a horizontal plane, for example in x-y-coordinates.

According to an embodiment, the handover position can be determined as being identical to the first position. This can correspond to a simple and reliable embodiment of the method.

According to an embodiment, determining the handover position can comprise moving the position determining device, by the gripping device, on the transport plane in each direction of a group of directions for a given amount of displacement, each moving starting from the first position, to a respective intermediate position; after each step of moving in a direction, moving the position determining device while being held by the gripping device to a respective further position by the attractive force; detecting each respective further position; and determining the handover position based on the first position and/or based on the respective further positions.

Such an implementation has been proven to increase the accuracy with which a position at which a sample container will be placed during operation is determined. Especially, due to the fact that the position determining device can be moved in each of a group of directions, a potential error that occurred due to a friction-induced stop at the first determination step can be avoided.

According to an embodiment, the group of directions can comprise two, three or four directions. Typically, an embodiment having four directions has been proven suitable.

According to an embodiment, all directions contained in the group of directions can be arranged with equal angle between each two circularly neighboring directions. This can allow for a simple and suitable arrangement of the directions. For example, if four directions are used, respective right angles can be present between each two neighboring directions.

According to an embodiment, the given amount of displacement can less than 10 mm in one embodiment, less than 5 mm in another embodiment, and less than 3 mm in yet another embodiment. Such values have been proven suitable for typical applications.

According to an embodiment, the handover position can be determined as a center of a polygon defined by the further positions. This can allow for a suitable determination of the handover position corresponding to an average value of the respective further positions.

It can be noted that it may not be necessary to move the position determining device back to the first position every time before moving the gripping device into the respective direction. It can also be moved directly to the respective intermediate position, which can be calculated.

According to an embodiment, the handover electro-magnetic actuator can be deactivated before each step of moving the position determining device in one of the directions and can be reactivated after the step. This can allow for movement of the position determining device by the gripping device without influence from a magnetic field generated by the electro-magnetic actuator.

According to an embodiment, this first position and/or the further positions can be represented by planar coordinates on the transport plane after being detected. Such planar coordinates can, for example, be determined by respective position sensors, which can, for example, be based on optical detection or laser-based distance measurements.

According to an embodiment, the step of positioning, by the gripping device, the position determining device on the transport plane can be performed such that the gripping device can be positioned over or beside the handover electro-magnetic actuator. This can correspond to a coarse positioning of the position determining device such that the remaining method steps can be performed in order to perform a fine positioning.

According to an embodiment, the step of positioning the position determining device, while being held by the gripping device, on the transport plane can be performed manually or by hand. This can allow for an efficient, fast and reliable placement of the position determining device on the intended electro-magnetic actuator at which the handover position can be determined.

According to an embodiment, electro-magnetic actuators surrounding the handover electro-magnetic actuator can be activated such that they can generate respective magnetic fields interacting with the magnetic field generated by the magnetically active device such that a repulsive force can be applied on the position determining device at least during each step of moving the position determining device by the attractive force. This can further improve the determination of the handover position, as has been shown by experiments.

According to an embodiment, the position determining device can comprise a number of rows, or ball-bearings, for contacting the transport plane. This can reduce friction between the position determining device and the transport plane and can thus improve the accuracy in determining of the handover position.

A magnetically active device can be positioned at a lower end of the position determining device. Such a magnetically active device can, for example, be a permanent magnet and can interact with magnetic fields generated by the electro-magnetic actuators. For example, the position determining device can be shaped similarly to a pen or similarly to a laboratory tube that can easily be gripped by the gripping device.

A laboratory automation system is presented. The laboratory automation system can comprise a plurality of analyzing stations, a number of gripping devices and a laboratory sample distribution system.

The laboratory sample distribution system can comprise a number of sample container carriers configured to carry one or more sample containers. Each sample container carrier can comprise at least one magnetically active device. It can further comprise a transport plane configured to support the sample container carriers. It can further comprise a number of electro-magnetic actuators stationary arranged in rows and columns below the transport plane. The electro-magnetic actuators can be configured to move a sample container carrier on top of the transport plane by applying a magnetic force to the sample container carrier.

The laboratory sample distribution system can further comprise a control device configured to control the movement of the sample container carriers on top of the transport plane by driving the electro-magnetic actuators such that the sample container carriers move along corresponding transport paths. Especially, the control device can be configured to activate the electromagnetic actuators such that the sample container carriers can move simultaneously and independently from one another along pre-calculated routes.

For each gripping device, a handover electro-magnetic actuator can be assigned out of the number of electro-magnetic actuators. A sample container can be handed over to or from the gripping device while a sample container carrier carrying the respective sample container is positioned above the handover electro-magnetic actuator.

The laboratory automation system can further comprise a process control unit. The process control unit can be configured to control the gripping device and the laboratory sample distribution system such that the above method can be performed.

By use of the laboratory automation system, the advantages as discussed above with respect to the method can be made use of for a laboratory automation system. With respect to the method, all embodiments and variations as discussed herein can be applied.

The sample containers can typically be designed as tubes made of glass or transparent plastic and typically can have an opening at an upper end. The sample containers can be used to contain, store and transport samples such as blood samples or chemical samples.

The transport plane can also be denoted as transport surface. The transport plane can support the sample container carriers, what can also be denoted as carrying the sample container carriers.

The electro-magnetic actuators can typically be built as electromagnets, having a solenoid surrounding a ferromagnetic core. These electro-magnetic actuators may be energized in order to provide for a magnetic field that can be used to move or drive the sample container carriers. The at least one magnetically active device in each sample container carrier may be a permanent magnet. Alternatively, or additionally, an electromagnet can be used.

The control device can typically be a microprocessor, a microcontroller, a field-programmable gate array, a standard computer, or a similar device. In a typical embodiment, the control device can comprise a processor and storage. Program code can be stored in the storage in order to control the behavior of the processor when the storage code is executed on the processor.

The same statements as just given with respect to the control device also apply to the process control unit. It can be noted that the process control unit and the control device can be separate entities, or they can be embodied in a single entity.

The sample container carriers can typically be configured to move in two dimensions on the transport plane. The electro-magnetic actuators may be arranged in two dimensions below the transport plane. The electro-magnetic actuators may be arranged in a grid or matrix having rows and columns along which the electro-magnetic actuators can be arranged.

The laboratory stations can, for example, be pre-analytical, analytical and/or post-analytical (laboratory) stations. The stations may be arranged adjacent to the laboratory sample distribution system.

Pre-analytical stations may be configured to perform any kind of pre-processing of samples, sample containers and/or sample container carriers.

Analytical stations may be configured to use a sample or part of the sample and a reagent to generate a measuring signal, the measuring signal indicating if and in which concentration, if any, an analyte exists.

Post-analytical stations may be configured to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

It can be noted that performing the method by the laboratory automation system can include manual operation, as has already been indicated above with respect to the method. For example, the laboratory automation system can be configured to display a signal to a user that a manual operation has to be performed.

According to an embodiment, the magnetically active device of the position determining device can generate a stronger magnetic field than each of the magnetically active devices of the sample container carriers. This can allow for a highly reliable determination of the handover position; as higher magnetic forces apply on the position determining device that can especially overcome holding forces exerted by the gripping device even when the gripping device is put into a released mode.

According to an optional embodiment, the gripping device can position the position determining device, while being held by the gripping device, on the transport plane. Then, the position determining device, while being held by the gripping device, can be moved to a rotor transport unit. Then, the rotor transport unit can move or rotate the position determining device, while being held by the gripping device, to one or more transfer positions allocated to the rotor transport unit, thus teaching the one or more transfer positions into a coordinate system of the gripping device.

According to an optional embodiment, the position determining device can be transferred over the transport plane to a specific position of the laboratory automation system known by the gripping device. In other words, the coordinates of the specific position can be known by the gripping device. The gripping device can then grip the position determining device and use the position determining device for teaching in one or more functional positions actually not known by the gripping device. In other words, the gripping device can grip the position determining device using known coordinates and then use the position determining device for teaching in coordinates of the functional positions.

Referring initially to FIG. 1, FIG. 1 shows a laboratory automation system 10. The laboratory automation system 10 can comprise a first laboratory station 20, a second laboratory station 30 and a laboratory sample distribution system 100. It can further comprise a gripping device 25, e.g. in the form of a pick-and-place device.

The laboratory sample distribution system 100 can comprise a transport plane 110. Below the transport plane 110, a plurality of electro-magnetic actuators 120 can be arranged. Each electro-magnetic actuator 120 can comprise a respective ferromagnetic core 125.

A number of position sensors 130, embodied as Hall-sensors, can be distributed over the transport plane 110.

The laboratory sample distribution system 100 can further comprise a plurality of sample container carriers 140. A sample container carrier 140 can carry a respective sample container 145, embodied as laboratory tube. It can be noted that only one laboratory sample container carrier 140 carrying a respective sample container 145 is shown in FIG. 1 for exemplary purposes. A typical sample distribution system 100 can comprise a plurality of such sample container carriers 140.

Each sample container carrier 140 can comprise a magnetically active device in the form of a permanent magnet that is not visible in FIG. 1. Thus, magnetic fields generated by the electro-magnetic actuators 120 can drive a sample container carrier 140 over the transport plane 110. Furthermore, the magnetic field generated by the permanent magnet of a sample container carrier 140 can be detected by the position sensors 130, so that a feedback regarding the position of a sample container carrier 140 can be obtained.

Both the electro-magnetic actuators 120 and the position sensors 130 can be electrically connected to a control device 150. The control device 150 can drive the electro-magnetic actuators 120 such that the sample container carriers 140 can move along corresponding transport paths. It can also determine the position of each sample container carrier 140.

The laboratory stations 20, 30 can be arranged adjacent to the transport plane 110. It can be noted that these two laboratory stations 20, 30 are only shown for exemplary purposes in FIG. 1, and that a typical laboratory automation system 10 can comprise a more than two laboratory stations 20, 30.

Adjacent to the first laboratory station 20, the gripping device 25 in the form of a robot arm can be provided. The gripping device 25 can currently carry a position determining device 27 in the form of a pen held in a vertical orientation. The position determining device 27 can comprise a magnetically active device in the form of a permanent magnet at its lower end. However, this permanent magnet is not visible in FIG. 1.

Just beside the first laboratory station 20, a specific one of the electro-magnetic actuators 120 can be defined as a handover electro-magnetic actuator 121. If a sample container 145 is to be brought to or collected from the first laboratory station 20, a sample container carrier 140 carrying the specific sample container 145 can be moved to and then held by the handover electro-magnetic actuator 121. The sample container 145 can be gripped by the gripping device 25 and can then be handed over to the first laboratory station 20. The same principle works basically in reverse order when a sample container 145 is to be collected from the first laboratory station 20 and is to be transported away by a sample container carrier 140.

When the first laboratory station 20 is placed adjacent to the laboratory sample distribution system 100 for the first time, the gripping device 25 can also be installed. Then, the gripping device 25 can be calibrated so that it can grip a sample container 145 contained in a sample container carrier 140 that has been moved on the handover electro-magnetic actuator 121. This can be done using the position determining device 27, as will be shown further below with respect to FIG. 2.

Figure 2:
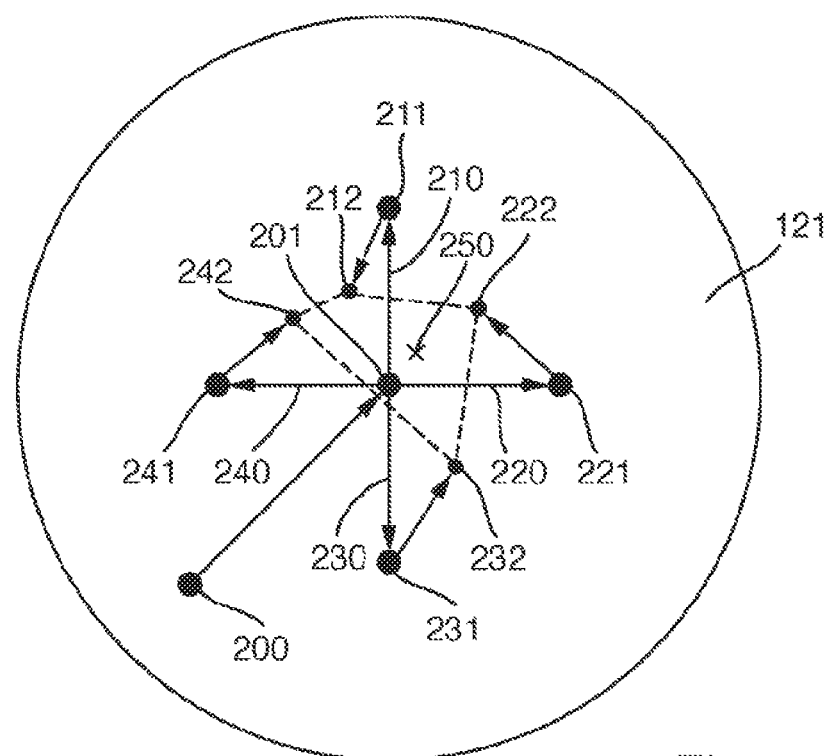
FIG. 2 illustrates typical steps in determining a handover position according to an embodiment of the present disclosure.

FIG. 2 shows a top view on the horizontal surface of the handover electro-magnetic actuator 121.

At first, the position determining device 27 can be placed manually at a starting position 200. The gripping device 25 can be put into a released state such that the position determining device 27 can move almost freely in a horizontal direction or plane while being held by the gripping device 25. Then the handover electro-magnetic actuator 121 can be activated, such that the position determining device 27 can be moved to a first position 201 due to the applied magnetic force.

In a very simple implementation of the method, the first position 201 can now be used as a handover position. However, in a refined implementation, the first position 201 can be used in order to further refine the handover position.

As shown in FIG. 2, a first direction 210, a second direction 220, a third direction 230 and a fourth direction 240 can each be defined starting at the first position 201. The four directions 210, 220, 230, 240 can be oriented rectangular with respect to each respective neighboring directions, and all displacements with respect to the first position 201 can have the same length.

The position determining device 27 can be moved in each of these four directions 210, 220, 230, 240 to respective intermediate positions 211, 221, 231, 241. It can be noted that these intermediate positions 211, 221, 231, 241 can be reached by action of the gripping device 25. Every time after having reached one of the respective intermediate positions 211, 221, 231, 241, the gripping device 25 can be released again such that the position determining device 27 can move essentially freely in horizontal direction. Then, the handover electro-magnetic actuator 121 can be activated in each case, and the position determining device can move to respective further positions 212, 222, 232, 242. This process can be repeated until all intermediate positions 211, 221, 231, 241 have been used.

The further positions 212, 222, 232, 242 can form a polygon that is shown in dashed lines in FIG. 2. This polygon can have a center, which can be denoted as a center of mass of a two-dimensional form. This center of mass can be calculated and taken as the handover position 250.

As is shown in FIG. 2, the handover position 250 being determined by this method can be different from the first position 201. In general, the handover position 250 as determined by the method just described can be more accurate than the first position 201.

If a sample container carrier 140 is moved to the handover electro-magnetic actuator 121, the gripping device can be moved to the handover position 250 and can thus grip correctly the sample container 145 contained in the sample container carrier 140.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of determining a handover position of a gripping device, wherein the gripping device is assigned to a laboratory sample distribution system having a transport plane and a plurality of electro-magnetic actuators positioned below the transport plane and wherein the handover position is assigned to a handover electro-magnetic actuator, the method comprising:
    grabbing, by the gripping device, a position determining device such that the position determining device is held fixedly by the gripping device, wherein the position determining device comprises a magnetically active device;
    positioning the position determining device, while being held by the gripping device, on the transport plane;
    activating the handover electro-magnetic actuator such that it generates a magnetic field interacting with a magnetic field generated by the magnetically active device such that an attractive force is applied on the position determining device;
    moving the position determining device, while being held by the gripping device, by the attractive force to a first position;
    detecting the first position; and
    determining the handover position based at least in part on the first position.

2. The method according to claim 1, wherein the handover position is determined as being identical to the first position.

3. The method according to claim 1, wherein determining the handover position comprises,
    moving the position determining device, by the gripping device, on the transport plane in each of a group of directions for a given amount of displacement, every time starting from the first position, to a respective intermediate position;
    after each step of moving in a direction, moving the position determining device while being held by the gripping device to a respective further position by the attractive force;
    detecting each respective further position; and
    determining the handover position based at least in part on the respective further positions.

4. The method according to claim 3, wherein the group of directions comprises two, three or four directions.

5. The method according to claim 3, wherein all directions contained in the group of directions are arranged with equal angle between each two circularly neighboring directions.

6. The method according to claim 3, wherein the given amount of displacement is less than 10 mm.

7. The method according to claim 3, wherein the given amount of displacement is less than 5 mm.

8. The method according to claim 3, wherein the given amount of displacement is less than 3 mm.

9. The method according to claim 3, wherein the handover position is determined as a center of a polygon defined by the further positions.

10. The method according to claim 3, wherein the handover electro-magnetic actuator is deactivated before each step of moving the position determining device in one of the directions and is reactivated after that step.

11. The method according to claim 3, wherein the first position and/or the further positions are represented by planar coordinates on the transport plane after being detected.

12. The method according to claim 1, wherein positioning, by the gripping device, the position determining device on the transport plane is performed such that the gripping device is positioned over or besides the handover electro-magnetic actuator.

13. The method according to claim 1, wherein positioning the position determining device, while being held by the gripping device, on the transport plane is performed manually.

14. The method according to claim 1, wherein electro-magnetic actuators surrounding the handover electro-magnetic actuator are activated such that they generate respective magnetic fields interacting with the magnetic field generated by the magnetically active device such that a repulsive force is applied on the position determining device at least during each step of moving the position determining device by the attractive force.

15. The method according to claim 1, wherein the position determining device comprises a number of rolls or ball-bearings for contacting the transport plane.

16. A laboratory automation system, the laboratory automation system comprising: a plurality of analyzing stations;
    a number of gripping devices;
    a position determining device fixedly held by at last one of the number of gripping devices;
    a laboratory sample distribution system comprising
    a number of sample container carriers configured to carry one or more sample containers, each sample container carrier comprising at least one magnetically active device,
    a transport plane configured to support the sample container carriers,
    a number of electro-magnetic actuators stationary arranged below the transport plane, the electro-magnetic actuators configured to move a sample container carrier on top of the transport plane by applying a magnetic force to the sample container carrier, and
    a control device configured to control the movement of the sample container carriers on top of the transport plane by driving the electro-magnetic actuators such that the sample container carriers move along corresponding transport paths, wherein for each gripping device, a handover electro-magnetic actuator is assigned out of the number of electro-magnetic actuators, wherein a sample container is to be handed over to or from the gripping device while a sample container carrier carrying the respective sample container is positioned above the handover electro-magnetic actuator; and a process control unit, wherein the process control unit is configured to control the gripping devices and the laboratory sample distribution system such that a method according to claim 1 is performed.

17. The laboratory automation system according to claim 16, wherein the magnetically active device of the position determining device generates a stronger magnetic field than each of the magnetically active devices of the sample container carriers.

* * * * *